(12) United States Patent
Leyshon

(10) Patent No.: US 6,562,987 B1
(45) Date of Patent: May 13, 2003

(54) METHOD FOR HIGHLY EXOTHERMIC EPOXIDATION REACTIONS

(75) Inventor: David W. Leyshon, West Chester, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/085,702

(22) Filed: Feb. 28, 2002

(51) Int. Cl.⁷ .............................................. C07D 301/19
(52) U.S. Cl. ....................................... 549/529
(58) Field of Search ......................................... 549/529

(56) References Cited

U.S. PATENT DOCUMENTS

| | | | |
|---|---|---|---|
| 3,351,635 A | 11/1967 | Kollar | 260/348.5 |
| 3,829,392 A | 8/1974 | Wulff | 252/430 |
| 3,923,843 A | 12/1975 | Wulff | 260/348.5 L |
| 4,021,454 A | 5/1977 | Wulff et al. | 260/348.3 L |
| 4,217,287 A * | 8/1980 | Yong-Wu et al. | 549/529 |
| 4,367,342 A | 1/1983 | Wulff et al. | 549/529 |
| 5,760,253 A | 6/1998 | Danner et al. | 549/529 |
| 5,849,937 A | 12/1998 | Jubin et al. | 549/529 |

FOREIGN PATENT DOCUMENTS

| | | |
|---|---|---|
| EP | 0 323 663 | 12/1988 |
| GB | 1249079 | 4/1970 |

* cited by examiner

Primary Examiner—Bernard Dentz
(74) Attorney, Agent, or Firm—William C. Long

(57) ABSTRACT

A process is provided for the production of oxirane compounds by reaction of an olefin such as propylene with an organic hydroperoxide using a solid contact catalyst, characterized in that a series of separate reaction zones are used, each packed with epoxidation catalyst, and the concentration of hydroperoxide in the feed to each reaction zone is maintained below 8 wt %.

4 Claims, 3 Drawing Sheets

FIG. 1  EFFECT OF DILUTION ON MULTIPLE STEADY STATES ADIABATIC PFR, K=100

METHOD FOR HIGHLY EXOTHERMIC EPOXIDATION REACTIONS

BACKGROUND OF THE INVENTION

1. Field of the Invention

The present invention relates to a process for carrying out a highly exothermic reaction such as that between an olefin and an organic hydroperoxide using a solid catalyst to form an oxirane compound.

2. Description of the Prior Art

Substantial difficulties are encountered in carrying out highly exothermic reactions where reactants and/or products are temperature sensitive. For example, the liquid phase reaction of propylene and an organic hydroperoxide using a solid catalyst to produce propylene oxide is a highly exothermic reaction, and selectivity to the desired product is very temperature sensitive. Proper control of reaction temperature presents a serious problem.

Conventional reactors for exothermic reactions are usually of two types:

(1) Quench type which consist of multiple fixed beds with cold feed quench injected in between beds
(2) Tubular type in which the catalyst is placed in the tubes of vertical shell and tube heat exchanger.

If the heat of reaction is high, the first type does not provide sufficient heat removal and proper reaction temperature control may not be possible.

The tubular reactor cost becomes prohibitive when high heats of reaction have to be removed through heat exchanger surfaces operating with a low heat transfer coefficient. There is also a temperature gradient from the center of the tube which is often detrimental to a process which requires nearly isothermal conditions.

Epoxidation can be carried out using multiple fixed catalyst bed reactors. The fixed bed epoxidation process may be practiced with a fresh bed last or fresh bed first rotation plan. See U.S. Pat. No. 5,849,937. Fresh bed first is preferable, since the downstream, older beds can be run at a higher temperature. This obtains the maximum activity at the best selectivity and with a minimum heat input and capital expense. One problem with fresh bed first however, is that of temperature control. The temperature rise for an adiabatic bed is large, about 150° F. or more and this results in rapid catalyst deactivation of the downstream portion of the bed. It also means that the front part of the bed, where the temperature is much cooler, is not converting very much product. A second problem is that the fixed bed reactors are very difficult to operate with normal reactant concentrations. If one wishes to obtain 30% to 50% hydroperoxide conversion, this is essentially impossible in an adiabatic bed because the reactor exhibits multiple steady states. One can obtain 1 to 15% hydroperoxide conversion or 99.0 to 99.9% conversion, but obtaining 30 to 50% hydroperoxide conversion is not possible.

To illustrate this, reference is made to FIG. 1 which is a plot of reaction inlet temperature versus hydroperoxide conversion for a conventional reaction system for propylene oxide production by reaction of propylene and ethylbenzene hydroperoxide. As can be seen, there is a steady increase in hydroperoxide conversion with increasing inlet temperature until an inlet temperature is reached at which hydroperoxide conversion jumps from a relatively low level to nearly 100%. When inlet temperature is then reduced, hydroperoxide conversion remains near 100% until at a substantially lower temperature hydroperoxide conversion suddenly falls to a much lower level. Under normal conditions, control of conversion at an intermediate level e.g. 50%, is almost impossible to accomplish. This can be seen from FIG. 1. When the inlet temperature is raised, the conversion suddenly jumps from 20 to 99%. Upon reducing the inlet temperature, the conversion suddenly drops from 99 to 2%.

BRIEF DESCRIPTION OF THE INVENTION

In accordance with the present invention, the exothermic reaction between an olefin such as propylene and an organic hydroperoxide such as ethylbenzene hydroperoxide using a solid catalyst is carried out while maintaining the concentration of hydroperoxide in the feed below 8 wt % by either diluting the feed with a process stream depleted in hydroperoxide or by using a plurality of epoxidation zones and feeding only a portion of the total hydroperoxide feed to each zone.

In accordance with one embodiment, the invention a reactor system is provided comprised of a series of reaction zones packed with solid catalyst. The reaction mixture from the first reaction zone is separated into two portions, one portion being recycled to the feed to the first zone, the remainder passing to the second zone. The recycled portion is admixed with cold feed thus both preheating and diluting the feed while moderating the temperature of the reaction mixture passing through the first reaction zone and permitting convenient control of reactant conversion at a desired intermediate level.

In accordance with another embodiment, again a series of reaction zones is used with a portion of the total hydroperoxide being fed to each zone.

DETAILED DESCRIPTION

Practice of the invention is especially applicable to highly exothermic reactions such as those between an olefin, e.g. propylene, and an organic hydroperoxide, e.g. ethylbenzene hydroperoxide.

Figure 1:
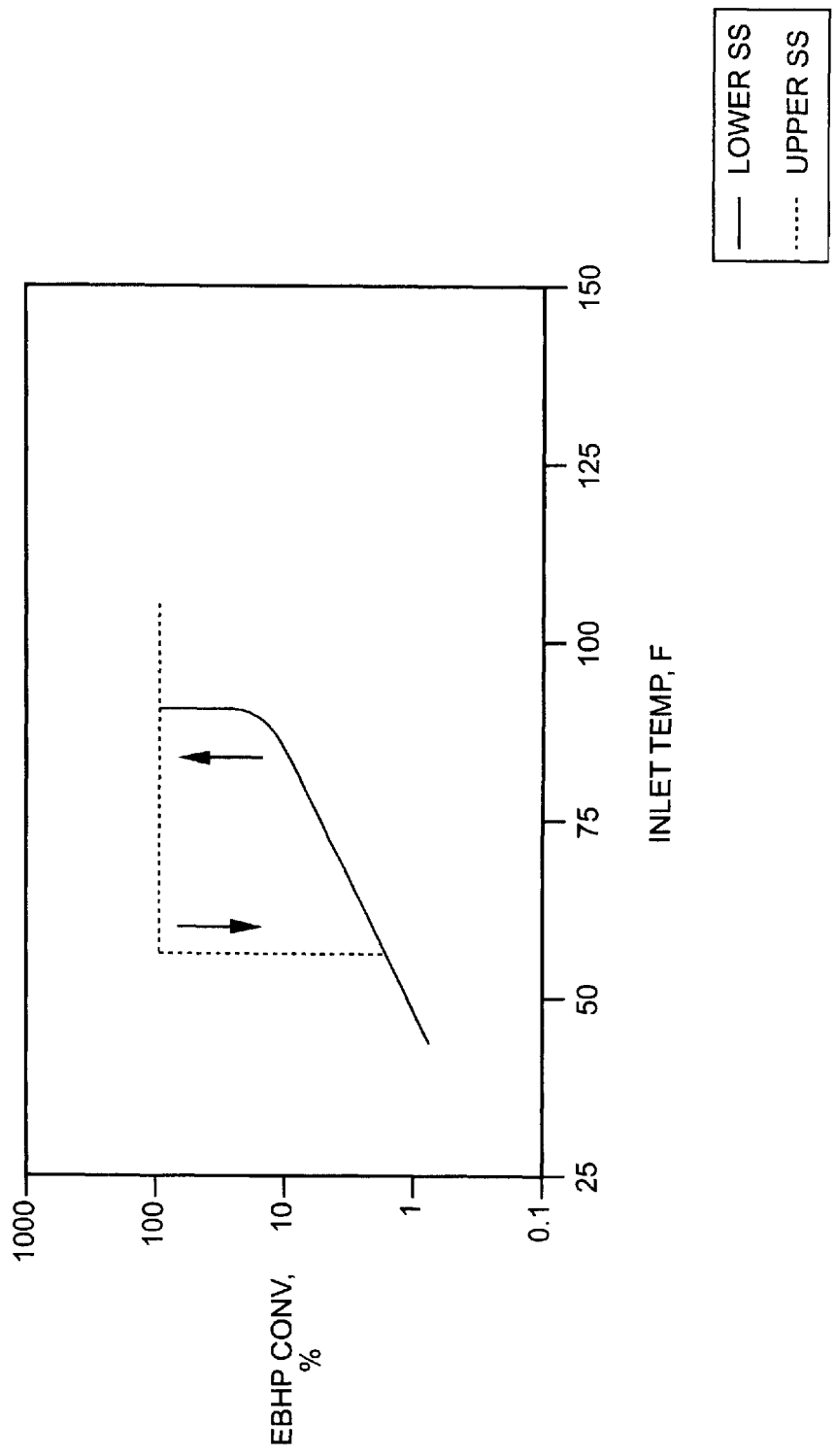
FIG. 1 is an illustrative plot of ethylbenzene hydroperoxide conversion versus feed inlet temperature for a typical system involving reaction of propylene and ethylbenzene hydroperoxide to form propylene oxide using a solid catalyst.
Figure 2:
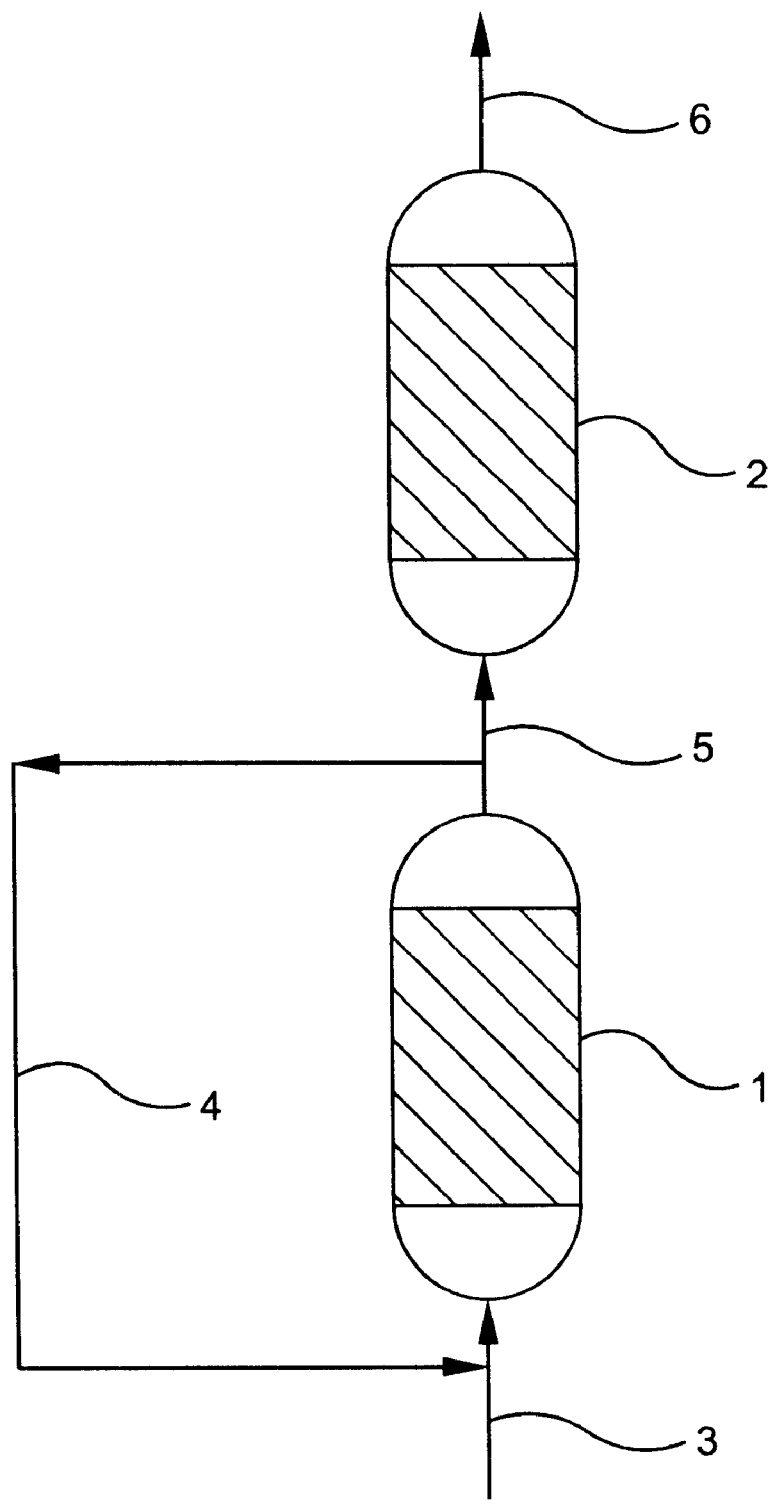
FIG. 2 illustrates a practice of the invention.

In order to illustrate the invention, reference is made to attached FIG. 2 in the context of the reaction of ethylbenzene hydroperoxide with propylene to form propylene oxide. There are provided reaction zones 1 and 2, each packed with a bed of solid epoxidation catalyst. A cold feed stream of ethylbenzene hydroperoxide and propylene is fed via line 3 to reactor 1. Also fed via lines 4 and 3 to reactor 1 is a portion of the effluent reaction stream recycled from reactor 1 which is admixed with the fresh cold feed in sufficient amount to reduce the hydroperoxide concentration in the total feed to reaction zone 1 from the normal 10–20 wt % to below 8 wt %.

In reactor 1, the exothermic reaction of the hydroperoxide and propylene takes place with the formation of propylene oxide. The reaction mixture passes from reactor 1 via line 5 with the net equivalent of the feed passing to reactor 2 and a portion being recycled via lines 4 and 3 as above indicated to reactor 1.

In reactor 2 the mixture introduced via line 5 reacts to form additional propylene oxide and the reaction effluent is removed from reactor 2 via line 6 and can be worked up in conventional fashion for propylene oxide recovery and recycle of unreacted materials.

Two separate reaction zones are illustrated in FIG. 2 but it will be understood additional reaction zones can be provided. Also, although separate reactors are illustrated it will be understood that other configurations such as a single reaction vessel containing multiple reaction sections can be employed.

It has been found that better catalyst life and selectivity is obtained in accordance with the invention by recycling effluent from the first reaction zone back to the feed in amount sufficient to reduce the hydroperoxide concentration to below 8 wt %. The temperature rise is reduced and this reduces the difference in the rates of catalyst deactivation. It also reduces the average temperature needed for a given conversion, thus increasing the selectivity. The reactor temperature is much easier to control since the rate of convective heat transfer through the bed is larger. In general, hydroperoxide conversion in the first reaction zone is regulated at about 20 to 99%. Sufficient recycle of the first reaction zone effluent to the first zone feed is provided to dilute the hydroperoxide concentration in the first zone feed from the normal 10 to 30 wt % to about 4 to 8 wt %.

Figure 3:
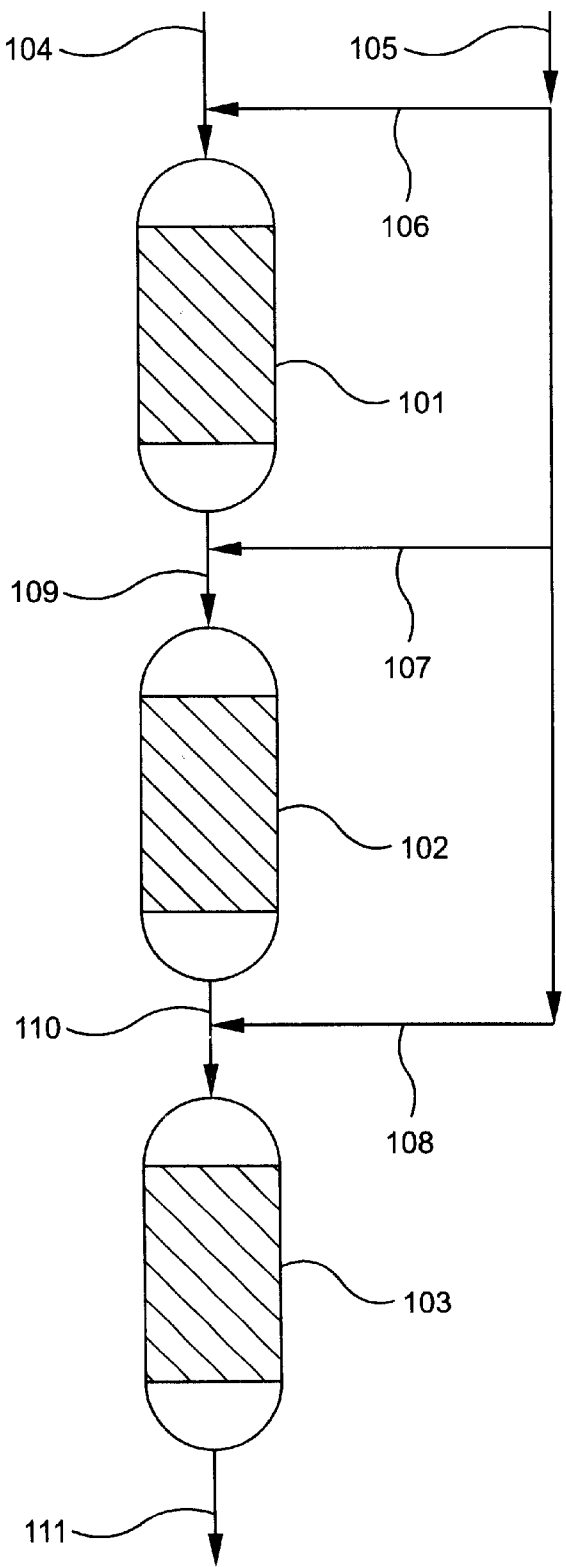
FIG. 3 illustrates an alternative practice of the invention.

An alternate embodiment of the invention is shown in FIG. 3, also in the context of the reaction of propylene with ethylbenzene hydroperoxide to form propylene oxide.

As shown in FIG. 3, there are provided reaction zones 101, 102 and 103, each packed with solid epoxidation catalyst. A propylene feed stream is fed to reactor 101 via line 104. An ethylbenzene hydroperoxide stream, preferably an oxidate stream from ethylbenzene oxidation is fed to the reaction system via line 105.

Normally in this reaction where all of the propylene and hydroperoxide are fed to the first reaction zone, the hydroperoxide concentration by weight is in excess of 10 wt %, usually 10 to 30 wt %. However, in accordance with the present invention as shown in FIG. 3, only a portion of the total hydroperoxide is fed to each of the reaction zones 101, 102 and 103 by lines 106, 107 and 108 respectively. The amount of hydroperoxide added via each of lines 106, 107 and 108 is regulated to provide a hydroperoxide concentration in the feed to each of zones 101, 102 and 103 of less than 8 wt %.

Propylene fed via line 104 and hydroperoxide fed via line 106 are reacted in zone 101 in contact with solid epoxidation catalyst to form propylene oxide.

The reaction mixture from zone 101 is removed via line 109, admixed with additional ethylbenzene hydroperoxide from line 107 to provide a feed to zone 102 comprised of less than 8 wt % hydroperoxide; and reacted in zone 102 to form additional propylene oxide.

Reaction effluent from zone 102 is removed via line 110 and admixed with additional hydroperoxide from line 108 to provide a feed to zone 103 comprised of less than 8 wt % hydroperoxide.

The reaction mixture from zone 103 is removed via line 111 and components thereof separated by conventional techniques.

Although three reaction zones are shown in FIG. 3, it will be appreciated that a greater or lesser number, e.g. 2 to 10 zones can be used.

Practice of the invention as above described allows close control of reaction conditions with accompanying improvement in reaction selectivity and catalyst life.

While it would be possible to lower the hydroperoxide concentration while adding all olefin and hydroperoxide to the reaction zone, such a procedure would result in substantially increased costs and difficulties in separations and recycle.

The epoxidation reaction of the present invention is carried out in accordance with known procedures. See, for example, U.S. Pat. No. 3,351,635, the disclosure of which is incorporated herein by reference for ppropriate temperatures, pressures, and reactants.

Generally reaction temperatures are in the range of 100° F. to 300° F., usually 150° F. to 250° F., and pressures are sufficient to maintain the liquid phase in both reactors 1 and 2, e.g. 500 to 1500 psia.

Known solid heterogeneous catalysts are employed. In this regard, reference is made to European patent publication 0 323 663, to UK 1,249,079, to U.S. Pat. Nos. 4,367,342, 3,829,392, 3,923,843 and 4,021,454 the disclosures of which are incorporated herein as well as to U.S. Pat. No. 5,760,253.

The invention is especially applicable to epoxidation of alpha olefins having 3–5 carbon atoms with aralkyl hydroperoxide.

The following examples illustrate an preferred practices of the invention.

EXAMPLE 1

Referring to Table 1 and FIG. 2, propylene and ethylbenzene hydroperoxide feed at about 110° C. and 1000 psia are introduced to zone 1 via line 3 at the rate of about $1.4 \times 10^6$ lbs/hr.

Also fed to zone 1 via lines 4 and 3 at the rate of $1.4 \times 10^6$ lbs/hr. is a portion of the first zone effluent as recycle.

The reaction mixture passes through the solid catalyst bed in reactor 1 and is removed therefrom via line 5.

The liquid reaction mixture is separated into a recycle stream which returns to reactor 1 via lines 4 and 3 and a net reaction stream which passes to reactor zone 2. Reaction zone 2 is also packed with the same titania on silica catalyst used in reactor 1. In reactor 2 further exothermic reaction of propylene with ethylbenzene hydroperoxide takes place to form propylene oxide.

Reactor 1 is a conventional reactor which contains a packed bed of titania on silica catalyst prepared as described in Example VII of U.S. Pat. No. 3,923,843. During passage through the catalyst bed in reactor 1 the exothermic reaction of propylene with ethylbenzene hydroperoxide takes place with the formation of propylene oxide. Pressure entering zone 1 is 1000 psia.

As a result of the reaction exotherm in zone 1, there is a rise in temperature of the reaction mixture of about 74° F.

The following Table 1 gives the weight percentage compositions for the various process streams. The Stream No. designation refers to the process stream in the corresponding line or zone in the attached FIG. 2.

TABLE 1

Reactor with Recycle

|  | Fresh Feed | Recycle | Net Product | Combined Feed |
|---|---|---|---|---|
| Stream No. | 3 | 4 | 6 | 3 + 4 |
| Temp, F. | 110 | 185 | 223 | 149 |
| Pressure, psig | 1000 | 1000 | 1000 | 1000 |
| Composition, wt % | | | | |
| PO | 0 | 5.9 | 5.9 | 5.9 |
| EBHP | 14.5 | 0.001 | .001 | 7.25 |
| C3= | 52.8 | 48.6 | 48.6 | 50.7 |
| MBA | 1.6 | 14.0 | 14.0 | 7.8 |
| ACP | 1.8 | 2.1 | 2.1 | 2.0 |

TABLE 1-continued

Reactor with Recycle

|  | Fresh Feed | Recycle | Net Product | Combined Feed |
|---|---|---|---|---|
| EB | 23.5 | 23.5 | 23.5 | 23.5 |
| Propane | 5.8 | 5.8 | 5.8 | 5.8 |
| Rate lb/hr | $1.4 \times 10^6$ | $1.4 \times 10^6$ | $2.8 \times 10^6$ | $2.8 \times 10^6$ |

EXAMPLE 2

Referring to FIG. 3, propylene and ethylbenzene feed at about 50° C. and 1000 psia are employed as starting materials. The entire amount of the propylene feed it passed by means of line 104 into the reactor 102 which is a fixed bed reactor containing an appropriate solid epoxidation catalyst. The totality of the ethylbenzene hydroperoxide feed stream to the system passes line 105 and is distributed respectively via line 106 to reactor 101 via line 107 to reactor 102 and via line 108 to reactor 103. The amount of ethylbenzene hydroperoxide introduced into each of the reaction zone feeds is controlled such that the concentration of hydroperoxide entering each of the three reactor zone is less that 8 wt % of the total feed to the respective zones.

In each of the reaction zones the feed mixture passes there through at reaction conditions with the formation of propylene oxide product. The reaction mixture from zone 101 passes via line 109 to zone 102. The appropriate amount of hydroperoxide is introduced line 107 and passes to zone 102 in admixture with the reaction effluent from zone 101. In zone 102, likewise reaction between hydroperoxide and propylene takes place with the formation propylene oxide product. Reaction effluent from zone 102 passes via line 110 to zone 103. Additional hydroperoxide is introduced via line 108 in admixture with the effluent from zone 102 such that the feed entering zone 103 likewise contains less than 8 wt % hydroperoxide. In zone 103 additional reaction between hydroperoxide and propylene takes place with the formation of propylene oxide.

Each of reaction zones 102, 103 and 104 contains a packed bed of titania on silica catalyst prepared as described in Example VII of U.S. Pat. No. 3,923,843. The following Table 2 gives the composition for the various process streams as well as the flow rates and temperatures and pressures occurring throughout the reaction system.

TABLE 2

Reactor with Split Feed

| Stream No. | 104 | 105 | 106 | 109 | 107 | 110 | 108 | 111 |
|---|---|---|---|---|---|---|---|---|
| Temp °, F. | 120 | 98 | 98 | 177 | 98 | 226 | 98 | 257 |
| Pressure, psig | 1000 | 1000 | 1000 | 1000 | 1000 | 1000 | 1000 | 1000 |
| Composition, wt % | | | | | | | | |
| PO | — | — | — | 2.7 | — | 4.5 | — | 5.8 |
| EBHP | — | 35.0 | 35.0 | 0.1 | 35.0 | 0.1 | 35.0 | 0.2 |
| C3= | 90.1 | — | — | 71.0 | — | 58.0 | — | 48.6 |
| MBA | — | 3.7 | 3.7 | 6.4 | 3.7 | 10.7 | 3.7 | 13.8 |
| ACP | — | 4.4 | 4.4 | 1.0 | 4.4 | 1.8 | 4.4 | 2.1 |
| EB | — | 56.8 | 56.8 | 10.8 | 56.8 | 18.2 | 56.8 | 23.5 |
| Propane | 9.8 | — | — | 8.0 | — | 6.7 | — | 5.8 |
| Rate lb/hr | 841094 | 592887 | 197619 | $1.04 \times 10^6$ | 197619 | $1.24 \times 10^6$ | 197619 | $1.43 \times 10^6$ |

I claim:

1. In a process for the catalytic liquid phase exothermic reaction of a $C_3$–$C_5$ olefin with an aryl alkyl hydroperoxide which comprises passing a mixture containing the olefin and hydroperoxide at reaction conditions of elevated temperature and pressure through a series of separate reaction zones each packed with a bed of solid epoxidation catalyst, the improvement wherein the liquid reaction mixture from the first reaction zone is divided into a first stream which is recycled to the first reaction zone and preheats the net feed thereto and a second stream which passes to the second reaction zone and is further reacted therein, the hydroperoxide concentration in the feed to each reaction zone being less than 8 wt %.

2. The process of claim 1 wherein propylene and ethylbenzene hydroperoxide are reacted to form propylene oxide.

3. The process of claim 1 wherein the solid catalyst is a titania on silica catalyst.

4. In a process for the catalytic liquid phase exothermic reaction of a $C_3$–$C_5$ olefin with an aryl alkyl hydroperoxide which comprises passing a mixture containing the olefin and hydroperoxicde at reaction conditions of elevated temperature and pressure through a series of separate reaction zones each packed with a bed of solid epoxidation catalyst the improvement wherein only a portion of the total hydroperoxide is fed to each reaction zone whereby the hydroperoxide concentration in the feed to each reaction zone is less than 8 wt %.

* * * * *